United States Patent
Wang

(10) Patent No.: US 8,076,064 B2
(45) Date of Patent: Dec. 13, 2011

(54) METHOD OF TREATMENT OF RNA SAMPLE

(75) Inventor: Hui Wang, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1202 days.

(21) Appl. No.: 11/177,679

(22) Filed: Jul. 9, 2005

(65) Prior Publication Data

US 2007/0009913 A1    Jan. 11, 2007

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......... 435/6; 435/91.1; 536/23.1; 536/24.3

(58) Field of Classification Search ............. 435/6, 91.1, 435/91.21, 91.51, 183; 436/94; 536/23.1, 536/24.3, 24.33, 25.1, 25.2, 25.3
See application file for complete search history.

(56) References Cited

U.S. PATENT DOCUMENTS

| | | | |
|---|---|---|---|
| 5,525,468 A | 6/1996 | McSwiggen | |
| 5,573,913 A | 11/1996 | Rosemeyer et al. | |
| 6,613,516 B1 * | 9/2003 | Christians et al. | 435/6 |
| 6,992,180 B1 | 1/2006 | Engelhardt et al. | |
| 7,288,371 B1 * | 10/2007 | Bavykin et al. | 435/6 |
| 2001/0014446 A1 | 8/2001 | Heroux et al. | |
| 2003/0190661 A1 | 10/2003 | Gruber et al. | |
| 2004/0180362 A1 | 9/2004 | Lazar et al. | |
| 2006/0160096 A1 | 7/2006 | Cole et al. | |

FOREIGN PATENT DOCUMENTS

| | | |
|---|---|---|
| WO | WO 94/12518 | 6/1994 |
| WO | WO0132672 A1 | 5/2001 |
| WO | WO0216647 A1 | 2/2002 |
| WO | WO2005054466 A2 | 6/2005 |

OTHER PUBLICATIONS

Zhulidov et al., Simple cDNA normalization using Kamchatks Crab duplex-specific nuclease. Nucleic Acids Research, 32, e37, 2004.*
The definition of microRNAs (miRNA) from Wikipedia, the free encyclopedia. Printed on Apr. 27, 2009.*
RNase H from Wikipedia, the free encyclopedia. Printed on Jan. 17, 2010.*
Liu, C., et al. An oligonucleotide microchip for genome-wide microRNA profiling in human and mouse tissues. PNAS 2004, vol. 101, No. 26, pp. 9740-9744.
Ularich Lehmann and Hans Kreipe.Real-time PCR analysis of DNA and RNA Extracted from Formalin-fixed and Praffin-Embedded Biopsies, Methods, 25, 409-418, 2001.
Richard Cosstick, et al., "Fluorescent labeling of tRNA and oligodeoxynucleotides using T4 RNA ligase", Nucleic Acids Research, vol. 12, No. 4, 1984, pp. 1791-1810.

(Continued)

*Primary Examiner* — Frank W Lu

(57) ABSTRACT

The invention relates to methods for treating samples of RNA. In an embodiment the method includes contacting the sample of RNA with an analogous DNA set to provide a DNA/RNA duplex. The analogous DNA set includes at least one sequence analogous to a small RNA. The method includes contacting the DNA/RNA duplex with an enzyme having a DNA:RNA nuclease activity to provide a digested RNA sample. Kits in accordance with the invention are also described.

18 Claims, 1 Drawing Sheet

OTHER PUBLICATIONS

Jorge R. Barrio, et al., "Synthesis of Modified Nucleoside 3', 5'-Bisphosphates and their Incorporation into Oligoribonucleotides with T4 RNA Ligase", Modified Oligoribonucleotides, vol. 17, No. 11, 1978 pp. 2077-2081.

Wang, H., et al., "Direct and sensitive miRna profiling from low-input total RNA", vol. 13, Nov. 14, 2006, pp. 1-9, XP002408565.

European Search Report EP 06 25 3554 dated Nov. 28, 2006.

"Kyle Cole, et al., Direct labeling of RNA with multiple biotins allows sensitive expression profiling of acute leukemia class predictor genes", Nucleic Research, vol. 32, No. 11 Oxford University Press 2004; pp. 1-9.

Volker Lohman, et al., "Mutations in Hepatitis C virus RNAs Conferring Cell Culture Adaptation", Journal of Virology, Vo. 75, No. 3, Feb. 2001, pp. 1437-1449.

Ross W. Richardson, et al., "Biotin and fluorescent labeling of RNA using T4 RNA ligase", Nucleic Acids Research, vol. 11, No. 18, 1983, pp. 6167-6184.

Thomas E. England, et al., Enzymatic Oligoribonucleotide Synthesis with T4 RNA Ligase, American Chemical Society and reprinted by permission of the copyright owner, Reprinted from Biochemistry, 1978 pp. 2070-2076.

Thomas England, et al., "3'-Terminal Labeling of RNA with T4 RNA Ligase", Nature, vol. 275, Oct. 1978; Department of Biochemistry, University of Illinois, pp. 560-561.

Lance A. Bare, et al., "Specific Substitution into the Anticodon Loop of Yeast Tyrosine Transfer RNA", Biochemistry 1986, 25, pp. 5825-5830; 1986 American Chemical Society.

A. Gregory Bruce, et al., "Reactions at the terminal tRNA with T4 RNA ligase", Nucleic Acids Research, vol. 5, No. 10, Oct. 1978, pp. 3665-3677.

Paul J. Romanuk, et al., "Joining RNA Molecules with RNA Ligase", Methods in Enzymology, vol. 100 pp. 52-59. XP001248219, 1983.

\* cited by examiner

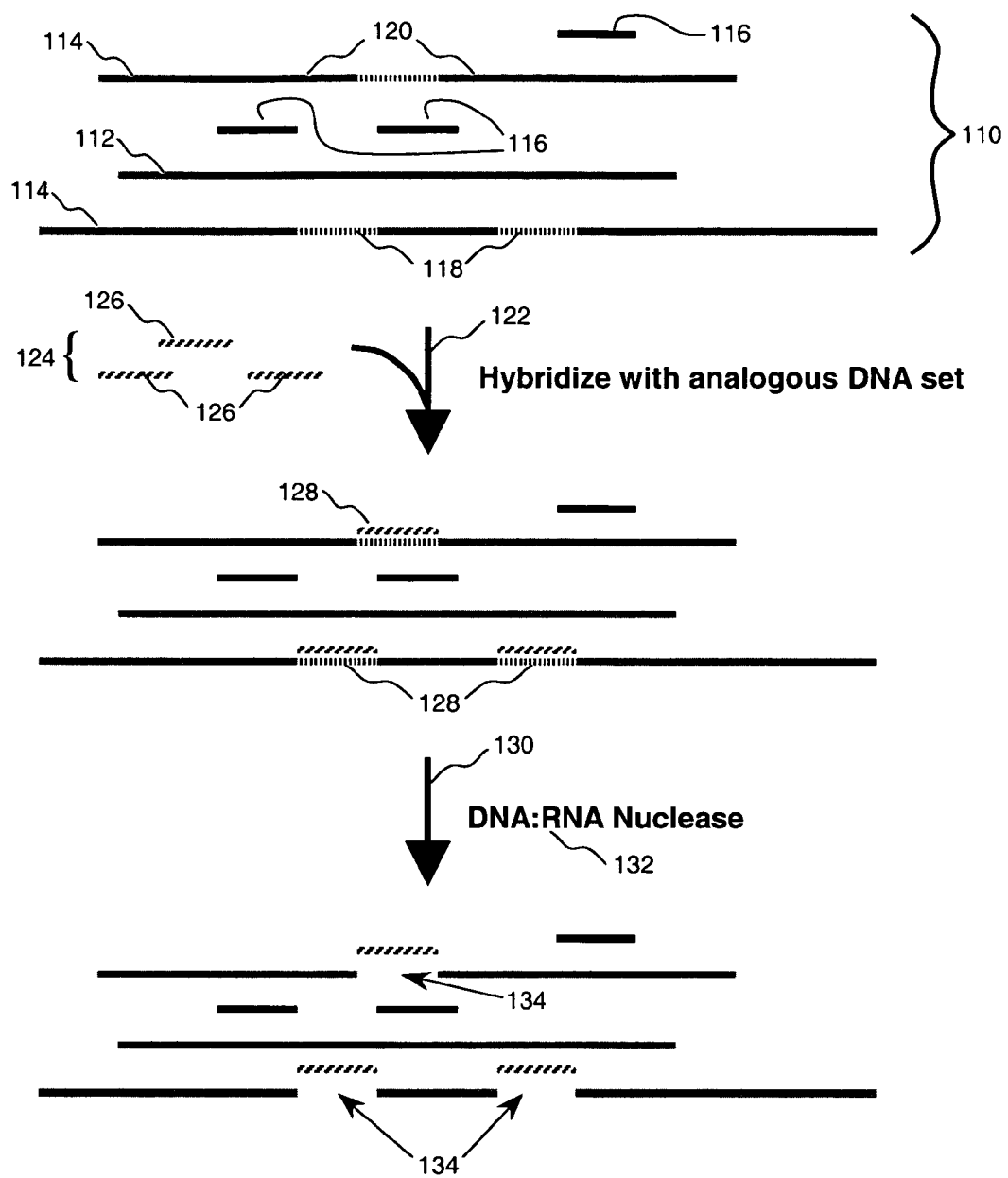
Figure

METHOD OF TREATMENT OF RNA SAMPLE

RELATED APPLICATIONS

Related subject matter is disclosed in a U.S. patent application Ser. No. 11/178,064 by Wang entitled "Microarray Analysis of RNA" co-filed with the present application.

FIELD OF THE INVENTION

The invention relates generally to methods of biochemical analysis. More specifically, the invention relates to a method of treating a sample of RNA to enhance analysis of the sample.

BACKGROUND OF THE INVENTION

There has been great interest in the analysis of small RNAs, such as short interfering RNAs (siRNAs), microRNAs (miRNA), tiny non-codingRNAs (mcRNA) and small modulatory RNA (smRNA), since the discovery of sRNA biological activity over a decade ago. See Novina et al., Nature 430: 161-164 (2004). Even though the functions of most discovered miRNAs remain a mystery, it has become clear that they exist in abundance in plants and animals, with up to tens of thousands of copies per cell. In the fruit fly, 78 have been identified, and over 200 have been identified in human (see the public database accessible via the website located at sanger.ac.uk/cqi-bin/Rfam/mirna/browse.pl). The levels of individual miRNAs seem to vary with developmental stages and tissue types. The level of fluctuation may be correlated with phenotype, mRNA levels, or protein levels for better biological insight. Thus quantitative measurements of miRNA may be of great importance. Further, viral miRNAs have been identified and may play a role in latency (see Pfeffer et al., Science, 304: 734-736 (2004)), making the detection and quantification of miRNAs a potentially valuable diagnostic tool.

Straightforward and reliable methods for simultaneously analyzing several constituents of a complex RNA sample are extremely desirable. While current methods of preparing RNA samples are quite useful, there is a continuing need for methods of preparing RNA samples for analysis or for other purposes.

SUMMARY OF THE INVENTION

The invention thus relates to novel methods for treating RNA samples. In one embodiment of the present invention, a method of treating a sample of RNA is provided wherein the method includes contacting the sample of RNA with an analogous DNA set to provide a DNA/RNA duplex. The analogous DNA set includes at least one sequence analogous to a small RNA. The method includes contacting the DNA/RNA duplex with an enzyme having a DNA:RNA nuclease activity to provide a digested RNA sample. The method may also include contacting the digested RNA sample with an enzyme having a DNA nuclease activity to result in digestion of the analogous DNA set.

Kits in accordance with the invention are also described, wherein the kits include an analogous DNA set and an enzyme having a DNA:RNA nuclease activity.

Additional objects, advantages, and novel features of this invention are set forth in part in the description follows and in part will become apparent to those skilled in the art upon examination of the following specifications or may be learned by the practice of the invention. The objects and advantages of the invention may be realized and attained by means of the instruments, combinations, compositions and methods particularly pointed out herein and in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein The FIGURE schematically illustrates embodiments of the present invention.

The FIGURE components are broadly illustrative and are not drawn to scale.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an oligodeoxynucleotide" includes a plurality of oligodeoxynucleotides. Similarly, reference to "an RNA" includes a plurality of different identity (sequence) RNA species.

Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. In this specification and in the claims that follow, reference will be made to a number of terms that shall be defined to have the following meanings unless a contrary intention is apparent.

"Optional" or "optionally" means that the subsequently described circumstance may or may not occur, so that the description includes instances where the circumstance occurs and instances where it does not. For example, if a step of a process is optional, it means that the step may or may not be performed, and, thus, the description includes embodiments wherein the step is performed and embodiments wherein the step is not performed (i.e. it is omitted).

An "oligonucleotide" is a molecule containing from 2 to about 100 nucleotide subunits. An "oligodeoxynucleotide" is a molecule containing from 2 to about 100 deoxyribonucleotide subunits. The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner similar to that of two naturally occurring nucleic acids, e.g., can participate in Watson-Crick base pairing interactions. The terms "nucleoside", "nucleotide", "oligodeoxynucleotide", and "deoxyribonucleotides" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Modified nucleosides or nucleotides also include molecules having structural features that are recognized in the literature as being mimetics, derivatives, having similar properties, or other like terms, and include, for example, polynucleotides incorporating non-natural (not usually occurring in nature) nucleotides, unnatural nucleotide mimetics such as 2'-modified nucleosides, peptide nucleic acids, oligomeric nucleoside phosphonates, and any polynucleotide that has added substituent groups, such as protecting groups or linking moieties.

A duplex is a double stranded structure typically formed between complementary nucleic acid sequences. A DNA/RNA duplex is a double stranded structure formed between a DNA molecule and an RNA molecule. Similarly, an RNA/RNA duplex is a double stranded structure formed between an RNA molecule and another RNA molecule (or different portions of the same RNA molecule).

"Sequence" may refer to a particular sequence of bases and/or may also refer to a polynucleotide having the particular sequence of bases. Thus a sequence may be information or may refer to a molecular entity, as indicated by the context of the usage.

"Moiety" and "group" are used to refer to a portion of a molecule, typically having a particular functional or structural feature, e.g. a linking group (a portion of a molecule connecting two other portions of the molecule), or an ethyl moiety (a portion of a molecule with a structure closely related to ethane). A moiety is generally bound to one or more other moieties to provide a molecular entity. As a simple example, a hydroxyl moiety bound to an ethyl moiety provides an ethanol molecule. At various points herein, the text may refer to a moiety by the name of the most closely related structure (e.g. an oligonucleotide moiety may be referenced as an oligonucleotide, a mononucleotide moiety may be referenced as a mononucleotide). However, despite this seeming informality of terminology, the appropriate meaning will be clear to those of ordinary skill in the art given the context, e.g. if the referenced term has a portion of its structure replaced with another group, then the referenced term is usually understood to be the moiety. For example, a mononucleotide moiety is a single nucleotide which has a portion of its structure (e.g. a hydrogen atom, hydroxyl group, or other group) replaced by a different moiety (e.g. a linking group, an observable label moiety, or other group). Similarly, an oligonucleotide moiety is an oligonucleotide which has a portion of its structure (e.g. a hydrogen atom, hydroxyl group, or other group) replaced by a different moiety (e.g. a linking group, an observable label moiety, or other group). "Nucleotide moiety" is generic to both mononucleotide moiety and oligonucleotide moiety.

"Linkage" as used herein refers to a first moiety bonded to two other moieties, wherein the two other moieties are linked via the first moiety. Typical linkages include ether(—O—), oxo(—C(O)—), amino(—NH—), amido(—N—C(O)—), thio(—S—), phospho(—P—), ester(—O—C(O)—).

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. "Free," as used in the context of a moiety that is free, indicates that the moiety is available to react with or be contacted by other components of the solution in which the moiety is a part.

"Isolated" or "purified" generally refers to isolation of a substance (compound, polynucleotide, protein, polypeptide, polypeptide, chromosome, etc.) such that the substance comprises a substantial portion of the sample in which it resides (excluding solvents), i.e. greater than the substance is typically found in its natural or un-isolated state. Typically, a substantial portion of the sample comprises at least about 2%, at least about 5%, at least about 10%, at least about 20%, at least about 30%, at least about 50%, at least about 80%, or at least about 90% of the sample (excluding solvents). For example, a sample of isolated RNA will typically comprise at least about 2% total RNA, or at least about 5% total RNA, where percent is calculated in this context as mass (e.g. in micrograms) of total RNA in the sample divided by mass (e.g. in micrograms) of the sum of (total RNA+other constituents in the sample (excluding solvent)). Techniques for purifying polynucleotides and polypeptides of interest are well known in the art and include, for example, gel electrophoresis, ion-exchange chromatography, affinity chromatography, and sedimentation according to density. In typical embodiments, the sample or the enzyme having a DNA:RNA nuclease activity is in isolated form; more typically, both are obtained in isolated form prior to use in the present methods.

The term "sample" as used herein relates to a material or mixture of materials, typically, although not necessarily, in fluid form, containing one or more components of interest.

The term "analyte" is used herein to refer to a known or unknown component of a sample. In certain embodiments of the invention, an analyte may specifically bind to a capture agent on a support surface if the analyte and the capture agent are members of a specific binding pair. In general, analytes are typically RNA or other polynucleotides. Typically, an "analyte" is referenced as a species in a mobile phase (e.g., fluid), to be detected by a "capture agent" which, in some embodiments, is bound to a support, or in other embodiments, is in solution. However, either of the "analyte" or "capture agent" may be the one which is to be evaluated by the other (thus, either one could be an unknown mixture of components of a sample, e.g., polynucleotides, to be evaluated by binding with the other). A "target" references an analyte.

The term "capture agent" refers to an agent that binds an analyte through an interaction that is sufficient to permit the agent to bind and concentrate the analyte from a homogeneous mixture of different analytes. The binding interaction may be mediated by an affinity region of the capture agent. Representative capture agents include polypeptides and polynucleotides, for example antibodies, peptides, or fragments of double stranded or single-stranded DNA or RNA may employed. Capture agents usually "specifically bind" one or more analytes.

The terms "specific binding", "specifically bind", or other like terms, refers to the ability of a capture agent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold). In certain embodiments, the binding constant of a capture agent and analyte is greater than $10^6$ $M^{-1}$, greater than $10^7$ $M^{-1}$, greater than $10^8$ $M^{-1}$, greater than $10^9$ $M^{-1}$, greater than $10^{10}$ $M^{-1}$, usually up to about $10^{12}$ $M^{-1}$, or even up to about $10^{15}$ $M^{-1}$.

The term "stringent assay conditions" as used herein refers to conditions that are compatible to produce binding pairs of nucleic acids, e.g., capture agents and analytes, of sufficient complementarity to provide for the desired level of specificity in the assay while being incompatible to the formation of binding pairs between binding members of insufficient complementarity to provide for the desired specificity. Stringent assay conditions are the summation or combination (totality) of both hybridization and wash conditions.

A "stringent hybridization" and "stringent hybridization wash conditions" in the context of nucleic acid hybridization (e.g., as in Southern or Northern hybridizations, or hybridization of molecules in solution) are sequence dependent, and are different under different experimental conditions. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1× SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions may affect the degree to which nucleic acids are specifically hybridized to complementary capture agents. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 1 to about 20 minutes; or, multiple washes with a solution with a salt concentration of about 0.1×SSC containing 0.1% SDS at 20 to 50° C. for 1 to 15 minutes; or, equivalent conditions. Stringent conditions for washing can also be, e.g., 0.2×SSC/0.1% SDS at 42° C. In instances wherein the nucleic acid molecules are oligodeoxynucleotides (e.g. oligonucleotides made up of deoxyribonucleotide subunits), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The term "pre-determined" refers to an element whose identity is known prior to its use. For example, a "pre-determined analyte" is an analyte whose identity is known prior to any binding to a capture agent. An element may be known by name, sequence, molecular weight, its function, or any other attribute or identifier. In some embodiments, the term "analyte of interest", i.e., a known analyte that is of interest, is used synonymously with the term "pre-determined analyte".

Interfering sequences: For convenience herein, sequences in a sample of RNA that are complementary to small RNAs are referenced as "interfering sequences".

Small RNA references RNAs less than about 500 bases long, e.g. less than about 400 bases long, less than about 300 bases long, less than about 200 bases long, less than about 100 bases long, less than about 60 bases long, less than about 50 bases long, less than about 40 bases long, or less than about 35 bases long. In particular embodiments, the small RNA may be selected from short interfering RNAs (siRNAs), microRNAs (miRNA), tiny non-coding RNAs (tncRNA) and small modulatory RNA (smRNA), or combinations thereof. See Novina et al., Nature 430: 161-164 (2004). In particular embodiments, small RNAs may be at least about 4 bases long, at least about 6 bases long, at least about 8 bases long, or longer.

"Complementary" references a property of specific binding between polynucleotides based on the sequences of the polynucleotides. As used herein, polynucleotides are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C. "Complementary" includes embodiments in which there is an absolute sequence complementarity, and also embodiments in which there is a substantial sequence complementarity. "Absolute sequence complementarity" means that there is 100% sequence complementarity between a first polynucleotide and a second polynucleotide, i.e. there are no insertions, deletions, or substitutions in either of the first and second polynucleotides with respect to the other polynucleotide (over the complementary region). Put another way, every base of the complementary region may be paired with its complementary base, i.e. following normal base-pairing rules. "Substantial sequence complementarity" permits one or more relatively small (less than 10 bases, e.g. less than 5 bases, typically less than 3 bases, more typically a single base) insertions, deletions, or substitutions in the first and/or second polynucleotide (over the complementary region) relative to the other polynucleotide. The complementary region is the region that is complementary between a first polynucleotide and a second polynucleotide (e.g. a target analyte and a capture agent; further e.g. an oligodeoxynucleotide that is analogous to a small RNA and an interfering sequence that is complementary to the small RNA). Complementary sequences are typically embedded within larger polynucleotides, thus two relatively long polynucleotides may be complementary over only a portion of their total length. The complementary region is typically at least about 10 bases long, more typically at least about 12 bases long, more typically at least about 15 bases long, still more typically at least about 20 bases long, or may be at least about 25 bases long. In various typical embodiments, the complementary region may be up to about 200 bases long, or up to about 120 bases long, up to about 100 bases long, up to about 80 bases long, up to about 60 bases long, up to about 45 bases long, or up to about 40 bases long.

Sequence complementarity between two nucleic acid molecules may expressed in terms of a percentage calculated as follows: When a corresponding position in a complementary sequence relative to a reference sequence is occupied by a complementary base (e.g. a base that would be expected to base pair with the base in the reference sequence), then the sequences are complementary at that position. The percent of sequence complementarity can be maximized by aligning the compared sequences alongside each other, sliding them back and forth relative to each other, and conservatively introducing gaps in the sequences where necessary. The percent of sequence complementarity is calculated by counting the number of complementary aligning residues dividing by the total length of the aligned region, including gaps in both sequences, and multiplying by 100. Sequence complementarity would thus be expressed as, e.g., "60% complementary over 40 bases," or "57% identity over 30 amino acids." In the example indicated below, the compared sequence ("Comp": (SEQ ID NO:1) sequence is 80% complementary over 44 bases compared to the reference ("Ref": (SEQ ID NO:2) sequence ((35 complementary bases/44 bases)×100%), where 44 is the total length of the aligned region, including gaps in both sequences.

sequence is complementary to the first RNA sequence. Analogous sequences may include DNA sequences that are 'absolutely analogous' to a given RNA sequence (i.e. do not have any base insertions, deletions, or substitutions relative to the given RNA sequence) as well as sequences that are 'substantially analogous' (i.e. having one or more relatively small (less than 10 bases, e.g. less than 5 bases, typically less than 3 bases, more typically a single base) base insertions, substitutions and/or deletions relative to the given RNA sequence over the analogous region). The analogous region is the region that is analogous between a DNA sequence and the given RNA sequence. Analogous sequences may be embedded within larger polynucleotides, thus a relatively long polynucleotide may have a portion that is analogous to a given RNA sequence, the portion being only a fraction of the total length of the polynucleotide. Similarly, the given RNA sequence may be only a fraction of the total length of the RNA molecule of which it is a part. The analogous region is typically at least about 10 bases long, more typically at least about 12 bases long, more typically at least about 15 bases long, still more typically at least about 20 bases long, or may be at least about 25 bases long. In various typical embodiments, the analogous region may be up to about 200 bases long, or up to about 120 bases long, up to about 100 bases long, up to about 80 bases long, up to about 60 bases long, up to about 45 bases long, or up to about 40 bases long.

An analogous sequence may have a percentage assigned to it as follows: when a corresponding position in an analogous DNA sequence relative to a given RNA sequence is occupied by an analogous base (e.g. A for A, G for G, C for C and T for U), then the sequences are analogous at that position. The percent of analogous sequence can be maximized by aligning the analogous DNA sequence and the given RNA sequence alongside each other, sliding them back and forth, and con-

```
Comp  UAUCCUCCAGUAACAUGUAAUGACGAAUGGAGGGUC--UUCUAAU  (SEQ ID NO: 1)  43 bases
      |||  ||||||||||   |||||||||||  |||||  |   |||                   35 compltry
Ref   AUA--AGGUCAUUGU---AUUACUGCUUACGACCCAGUAUAGUUA  (SEQ ID NO: 2)  40 bases
```

Note that the same sequences below (SEQ ID NO: 1 and SEQ ID NO:2) may also be used to show that the DNA sequence is 90% analogous sequence over 31 bases.

servatively introducing gaps in the sequences where necessary to account for insertions and deletions. The percent of analogous sequence is calculated by counting the number of

```
Comp  UAUCCUCCAGUAACAUGUAAUGACGAAUGGAGGGUC--UUCUAAU  (SEQ ID NO: 1)  43 bases
      |||  ||||||||||   |||||||||||  |||||                            28 compltry
Ref   AUA--AGGUCAUUGU---AUUACUGCUUACGACCCAGUAUAGUUA  (SEQ ID NO: 2)  40 bases
```

As used herein in the context of nucleotide sequences, 'analogous' references a DNA sequence that has the same sequence of bases as a given RNA sequence, except that T's in the DNA sequence substitute for U's in the RNA sequence. In particular embodiments in accordance with the present invention, a DNA sequence analogous to a first RNA sequence specifically hybridizes to a second RNA sequence under a given set of experimental conditions, such as using stringent hybridization conditions (or other conditions allowing for specific binding to occur), wherein the second RNA complementary aligning residues, dividing by the total length of the aligned region, including gaps in both sequences, and multiplying by 100. Percent analogous sequence would thus be expressed as, e.g., "60% analogous sequence over 40 bases," or "57% analogous sequence over 30 amino acids." In the example indicated below, the DNA sequence (SEQ ID NO:3) is 75% analogous sequence over 44 bases compared to the RNA sequence (SEQ ID NO:4) ((33 bases/44 bases)× 100%), where 44 is the total length of the aligned region, including gaps in both sequences.

```
DNA  ATA--AGGTCATTGT--ATTACTGCTTACGACCCAGTATAGTTA   (SEQ ID NO: 3)   40 bases
     |||  |||||||||||   ||  ||||||||||||| |||||   |||                33 analog.
RNA  AUACCAGGUCAUUGUUGAUUGCUGCUUACGU-CCAG-AACAUUA   (SEQ ID NO: 4)   42 bases
```

Note that the same sequences below (SEQ ID NO:3 and SEQ ID NO:4) may also be used to show that the DNA sequence is 84% analogous sequence over 31 bases.

```
DNA  ATA--AGGTCATTGT--ATTACTGCTTACGACCCAGTATAGTTA   (SEQ ID NO: 3)   40 bases
     ||||||||||   |||  |||||||||   ||||                               26 analog.
RNA  AUACCAGGUCAUUGUUGAUUGCUGCUUACGU-CCAG-AACAUUA   (SEQ ID NO: 4)   42 bases
```

Accordingly, in one embodiment of the present invention, a method of treating a sample of RNA is provided. The method includes contacting the sample of RNA with an analogous DNA set to provide a DNA/RNA duplex. The analogous DNA set includes at least one sequence analogous to a small RNA. The method includes contacting the DNA/RNA duplex with an enzyme having a DNA:RNA nuclease activity to provide a digested RNA sample.

The FIGURE illustrates an embodiment of a method in accordance with the present invention. As shown in the FIGURE, a sample of RNA 110 may include a variety of RNA molecules, including RNA molecules that lack any sequences complementary to small RNAs 112, RNA molecules that have one or more sequences complementary to small RNAs 114, and small RNAs 116. Sequences that are complementary to small RNAs are indicated at feature 118 (referenced as 'interfering sequences' herein), and sequences that are not complementary to small RNAs are indicated at feature 120. The sample of RNA 110 is then contacted 122 with an analogous DNA set 124. The analogous DNA set includes one or more oligodeoxynucleotides 126, each of the one or more oligodeoxynucleotides 126 comprising a sequence analogous to a corresponding small RNA. The oligodeoxynucleotides 126 hybridize to sequences that are complementary to small RNAs 118 (interfering sequences) to result in DNA/RNA duplexes 128. The DNA/RNA duplexes 128 are then contacted 130 with an enzyme having a DNA:RNA nuclease activity 132 to result in cleavage 134 of sequences that are complementary to small RNAs (interfering sequences), thereby providing a digested RNA sample.

Conditions under which the sample of RNA 110 is contacted 122 with an analogous DNA set 124 are selected to favor DNA/RNA duplex 128 formation over RNA/RNA duplex formation (e.g. resulting from small RNAs 116 in the sample of RNA 110 binding to the sequences that are complementary to small RNAs 118 (interfering sequences)). Such conditions typically may be provided by adjusting the concentration of the analogous DNA set 124 to be in molar excess over the small RNAs 116 present in the sample when the sample of RNA 110 is contacted with the analogous DNA set 124. Appropriate concentrations of the oligodeoxynucleotides 126 in the analogous DNA set 124 may be readily determined given the disclosure herein and ordinary skill in the art, for example, by running a group of dilution experiments to determine what concentration of the components provides acceptable results. The temperature and buffer composition are selected to provide for stable DNA/RNA duplex 128 formation between the oligodeoxynucleotides 126 and the complementary sequences 118 in the sample of RNA 110. Certain embodiments favor formation of the DNA/RNA duplex over formation of RNA/RNA duplex to provide for greater differentiation in binding to the interfering sequences. In such embodiments, digestion of the interfering sequences with the enzyme having the DNA:RNA nuclease activity will be favored. In some such embodiments the analogous DNA set may include an oligodeoxynucleotide that binds more tightly to an interfering sequence than the corresponding small RNA will. For example, the oligodeoxynucleotide may have fewer insertions, deletions, or substitutions relative to the interfering sequence than the corresponding small RNA has relative to the interfering sequence. As an example, a DNA/RNA duplex is made up of an oligodeoxynucleotide and an interfering sequence; and the interfering sequence may alternatively form an RNA/RNA duplex with the corresponding small RNA. If the small RNA has less sequence complementarity to the interfering sequence than the oligodeoxynucleotide does to the interfering sequence, it may be expected that formation of the DNA/RNA duplex may be favored over the RNA/RNA duplex, given an appropriate selection of hybridization conditions, e.g. stringent conditions. In this context "less sequence complementarity" references a lower percent sequence complementarity over a given number of bases, wherein the given number is typically an integer selected from the range from about 8 to about 45. As another example, in order to select an oligodeoxynucleotide that binds more tightly to an interfering sequence than the corresponding small RNA does, known sequence information (e.g. from a genomic database of the organism being investigated) about the small RNA and putative interfering sequence(s) is compared to design an oligodeoxynucleotide that selectively binds to the putative interfering sequence(s). Such selection and design of an oligodeoxynucleotide will be apparent from the description herein and need not be further discussed. In certain embodiments, selection of oligodeoxynucleotides may be based on experimental observation of binding to interfering sequences.

In typical embodiments, the DNA/RNA duplex is contacted with enzyme having the DNA:RNA nuclease activity to provide a digested RNA sample. This contacting is done under conditions sufficient to allow the enzyme to contact the DNA/RNA duplex and to cleave the RNA strand of the DNA/RNA duplex to provide the digested RNA sample. Under typical conditions in exemplary embodiments, the digested RNA sample will have RNA with fewer interfering sequences (e.g. sites complementary to and capable of binding to small RNA) compared to the sample of RNA. After the digested RNA sample is obtained, it may be analysed by any known method for analyzing samples containing RNA. Conditions for contacting the DNA/RNA duplex with the enzyme having the DNA:RNA nuclease activity are typically known in the literature or are routine and may also typically be obtained from the supplier of the enzyme having the DNA:RNA nuclease activity.

The enzyme having the DNA:RNA nuclease activity may be any enzyme known to be capable of specifically cleaving at DNA/RNA duplexes. The enzyme having a DNA:RNA nuclease activity should be selected such that the enzyme is capable of digesting at least a portion of the RNA molecule at the site of the DNA/RNA duplex (i.e. the portion of the sequence of the RNA molecule that is complementary to the DNA and is bound to the DNA via base-pairing interaction). "Digesting" in this regard references a cleavage of one or more internucleotide bonds in the RNA molecule at the site of the DNA/RNA duplex. "DNA:RNA nuclease activity" refers to an activity of an endoribonuclease that specifically hydrolyzes the phosphodiester bonds of RNA which is hybridized to DNA, but does not digest single or double-stranded RNA. Selection of the enzyme having a DNA:RNA nuclease activity will typically be based on availability of the enzyme and activity of the enzyme under the desired reaction conditions for the formation of the DNA/RNA duplex and the digestion of the RNA at the RNA/DNA duplex by the enzyme (e.g. temperature, pH, ionic strength, source of RNA, structural feature of RNA, concentration of RNA, presence of other materials (e.g. contaminants, salt, surfactant, other solvents) etc.) In typical embodiments, the enzyme having an DNA:RNA nuclease activity does not cause substantial digestion of RNA that is not part of a DNA/RNA duplex, i.e. the nuclease activity is specific for the DNA/RNA duplex. In this regard, "substantial digestion" refers to a loss of greater than 50% of observable signal relative to a control experiment under essentially similar conditions using an enzyme that does not cause digestion of RNA that is not part of a DNA/RNA duplex.

A typical example of such an enzyme having the DNA:RNA nuclease activity is RNase H, available from Pharmacia (Piscataway, N.J.). In certain embodiments, a thermostable enzyme having the DNA:RNA nuclease activity is employed, such an enzyme is HYBRIDASE thermostable RNase H, available from Epicentre (Madison, Wis.), or an RNase H obtained from *Thermus thermophilus*. See Guatelli et al., Proc. Nat. Acad. Sci. (1990) 87:1874-78; Bekkaoui et al., BioTechniques (1996) 20: 240-48. In particular embodiments, however, a non-thermostable enzyme is selected, allowing inactivation of the enzyme by a relatively simple heat treatment once the digestion of the DNA/RNA duplex is conducted. Thus, in some embodiments, a method in accordance with the present invention may include inactivating or removing the enzyme having the DNA:RNA nuclease activity after the enzyme has cleaved the DNA/RNA duplexes to provide the digested RNA sample, such as by heat inactivation or by using precipitation methods, chromatography methods, or other purification methods to effect a separation of the RNA in the RNA sample from the enzyme having the DNA:RNA nuclease activity.

RNase H is known to require as few as four paired bases in a DNA/RNA duplex to act as an endonuclease, thus the oligodeoxynucleotides of the analogous DNA set should each be at least four bases long. This may of course vary depending on the specific enzyme used. In typical embodiments, an oligodeoxynucleotide will be at least about 8 bases long, or at least about 10 bases long, or at least about 12 bases long, or at least about 14 bases long. In typical embodiments, an oligodeoxynucleotide may be up to about 20 bases long, or up to about 25 bases long, or up to about 30 bases long, or even longer, such as up to about 50 bases long, or up to about 100 bases long, or more. In certain embodiments, a single oligodeoxynucleotide may include a plurality of sequences analogous to small RNAs (e.g. concatenated together, optionally including 'spacer' sequences between the sequences analogous to small RNAs), wherein each of the plurality of sequences may be analogous to the same or different small RNAs.

In usual embodiments, the analogous DNA set comprises at least one sequence analogous to a small RNA. The small RNA is typically selected from the group consisting of a short interfering RNA (siRNA), microRNA (miRNA), tiny non-coding RNA (tncRNA) and a small modulatory RNA (smRNA). In certain embodiments, the small RNA is selected from an RNA that is less than about 100 bases long, e.g. less than about 60, 50, 40, 35 bases long. Typically the small RNA is at least about 10 bases long, more typically at least about 12 bases long, or at least about 15 bases long, or longer, although sizes or types of small RNAs other than those listed in this paragraph may be included in some embodiments in accordance with the present invention.

The analogous DNA set typically includes at least one, two, three, four, five, or more different oligodeoxynucleotides. In particular embodiments, each oligodeoxynucleotide comprises at least one sequence analogous to a small RNA. In some embodiments, the analogous DNA set includes at least 10, 15, 20, 25, 30, 40 or 50 different oligodeoxynucleotides, and may have up to about 100, 200, 300, 400, 1000 or more different oligodeoxynucleotides. In certain embodiments, the analogous DNA set includes oligodeoxynucleotides that are analogous to at least 5 different small RNAs. In an embodiment, the analogous DNA set is synthesized on a solid support followed by cleaving the synthesized DNA from the support. As an example, many different oligodeoxynucleotides may be synthesized in parallel, e.g. on a solid planar support or in multiwell plate holding insoluble supports such as beads, where the oligodeoxynucleotides are bound to the support(s) by a cleavable linker. See, e.g., Pon, R T, et al., Nucleic Acids Res. 32:923-631 (2004). When the synthesis is complete, the cleavable linker may be cleaved to release the set of oligodeoxynucleotides into solution. The solution containing the set of oligodeoxynucleotides is then recovered and used as a source of the analogous DNA set.

As mentioned herein, the analogous sequences may include one or more base insertions, deletions and/or substitutions relative to the small RNA. In particular embodiments, the analogous DNA set comprises at least one oligodeoxynucleotide comprising a sequence analogous to a small RNA, wherein the sequence includes one or more base insertions, deletions and/or substitutions relative to the small RNA.

In particular embodiments, the oligodeoxynucleotides of the analogous DNA set are selected such that the DNA/RNA duplexes formed will have similar thermal stabilities. The melting temperature ('$T_m$') of the DNA/RNA duplexes should be high enough to eliminate or reduce any non-specific binding (e.g. preventing non-complementary sequences from forming double-stranded structures). In such embodiments, the melting temperatures of at least 80% of the DNA/RNA duplexes will be within about 15° C. of each other, typically within about 12° C. of each other, about 10° C. of each other, or about 5° C. of each other. In such embodiments, the DNA/RNA duplexes have a melting temperature for their respective targets in a range of about 15° C., within about 10° C., or within about 5° C. of each other. In certain embodiments, the difference between the maximum and minimum melting temperatures is less than about 20° C., less than about 15° C., less than about 10° C., or less than about 5° C. In some embodiments, oligodeoxynucleotide sequences may be selected based on experimental determinations of their melting temperatures or calculations of their theoretical melting temperatures; or putative oligodeoxynucleotide sequences may first be selected based on calculations of their theoretical melting temperatures and then be confirmed experimentally. Methods for determining the melting temperature of nucleic acid duplexes are known in the art. See for example, Sambrook and Russell (2001) Molecular Cloning: A Laboratory Handbook, 10.38-10.41 and 10.47, which is incorporated by reference in its entirety.

A value for melting temperature can be determined mathematically using equations and algorithms known in the art. For duplex oligonucleotides shorter than 25 bp, "The Wallace Rule" can be used in which:

$$T_m(\text{in }°\text{C.}) = 2(A+T) + 4(C+G), \text{ where}$$

(A+T)—the sum of the A and T residues in the oligonucleotide, (C+G)—the sum of G and C residues in the oligonucleotide (see Wallace et al., Nucleic Acids Res. (1979) 6: 3543-3557). Computer programs for estimating $T_m$ are also available (see, e.g., Le Novere, Bioinformatics (2001) 17(12): 1226-1227). VisualOmp (DNA Software, Inc., Ann Arbor, Mich.) is an example of commercially available software for calculating nucleic acid duplex melting temperature.

A method in accordance with the present invention may further include contacting the digested RNA sample with an enzyme having a DNA nuclease activity to result in digestion of the analogous DNA set. "DNA nuclease activity" refers to an activity of an endonuclease that nonspecifically cleaves DNA, including cleaving single stranded DNA and double stranded DNA, but does not digest single or double-stranded RNA. Selection of the enzyme having a DNA nuclease activity will typically be based on availability of the enzyme and activity of the enzyme under the desired reaction conditions for the digestion of the DNA by the enzyme (e.g. temperature, pH, ionic strength, presence or concentration of RNA, presence of other materials (e.g. contaminants, salt, surfactant, other solvents) etc.) In typical embodiments, the enzyme having a DNA nuclease activity does not cause substantial digestion of RNA, i.e. the nuclease activity is specific for the DNA. One example of an enzyme having a DNA nuclease activity is DNase I, available from Pharmacia, although other enzymes having DNA nuclease activity may be selected instead. In some embodiments, the analogous DNA set may compete with the small RNAs in the digested RNA sample for binding sites that are complementary for small RNAs. Digestion of the analogous DNA set reduces the competition, enabling a more sensitive assay for the small RNAs in the digested RNA sample. Conditions employed for contacting the digested RNA sample with an enzyme having a DNA nuclease activity are typically known in the art, and need not be further detailed here. Other experimental parameters may be selected based on known ranges for the experimental parameters or determined through routine experimentation based on, e.g. efficacy of the digestion reaction. Such other experimental parameters may include, e.g. temperature, pH, ionic strength, source of RNA and/or enzyme, structural feature of RNA, concentration of RNA, concentration of DNA, presence of other materials (e.g. contaminants, salt, surfactant, other solvents) etc.

The sample of RNA may be obtained from any source. For example, the sample of RNA may be any RNA sample, typically a sample containing RNA that has been isolated from a biological source, e.g. any plant, animal, yeast, bacterial, or viral source, or a non-biological source, e.g. chemically synthesized. In particular embodiments, the sample of RNA includes one or more short RNAs, such as e.g. short interfering RNAs (siRNAs), microRNAs (miRNA), tiny non-coding RNAs (tncRNA) and small modulatory RNA (smRNA). See Novina et al., Nature (2004) 430: 161-164. In particular embodiments, the sample includes isolated small RNAs, e.g. the sample results from an isolation protocol for small RNA such as one or more of those listed in this paragraph. In certain embodiments, the small RNA targets may include isolated miRNAs, such as those described in the literature and in the public database accessible via the website located at sanger.ac.uk/cgi-bin/Rfam/miRNA/browse.pl. In particular embodiments, the sample includes isolated small RNAs, e.g. the sample results from an isolation protocol for small RNA, especially RNAs less than about 500 bases long, e.g. less than about 400 bases long, less than about 300 bases long, less than about 200 bases long, less than about 100 bases long, or less than about 50 bases long. In some embodiments, the sample of RNA may be a whole RNA fraction isolated from a biological source and includes messenger RNA and small RNA. Such samples including a diverse set of RNAs, such as a whole RNA fraction, may be referenced herein as "complex" RNA samples.

In certain embodiments, the invention may further include providing an observable label that may be observed to obtain information relating to the sample of RNA, such as the presence of particular sequences of RNA present in the sample. The observable label may be any observable label known in the art, e.g. a chromophore, a fluorescent label, a spin label, a radioisotope label, a mass label, a sequence label, a chemically reactive tag, an affinity label, or any other known label. In particular embodiments, the observable label is a fluorophore selected from the group consisting of Cy3, Cy5, and an Alexa dye. Further examples of observable labels include any commercially available fluorophores that can be conjugated to mononucleotides or polynucleotides, e.g. dyes from Molecular Probes (Eugene, Oreg. and Leiden, The Netherlands) such as the Alexa Fluor series (example: Alexa 350, Alexa 430, Alexa 532, Alexa 546, Alexa 568, and Alexa 594) rind the series of BODIPY conjugates. Other examples include: Tamra, Fluorescein, carboxyfluorescene, rhodamine, carboxyrhodamine, CY series, Oyster series, 6-carboxy-2',4',7',4,7-hexachlorofluorescein (HEX), 6-carboxy-4,5'-dichloro-2',7'-dimethoxyfluorescein (JOE or J), N,N,N',N'-tetramethyl-6-carboxyrhodamine(TAMRA or T), and 6-carboxy-X-rhodamine (ROX or R). More information about commercially available dyes for oligonucleotide conjugation can be found at the website located at synthegen.com. Any such dyes may potentially be used in accordance with the methods described herein. Such labels typically are well known in the art.

In particular embodiments, the RNA in the sample may already be labeled when the sample is obtained, e.g. the sample may be isolated from an organism grown in a radiolabeled medium. In an embodiment, the sample of RNA comprises RNA that has an observable label attached thereto, and this labeled sample of RNA is then contacted with an analogous DNA set to provide a DNA/RNA duplex. In particular embodiments, the RNA may be labeled by following a known labeling protocol. In some such embodiments, before the sample of RNA is contacted with the analogous DNA set, the sample of RNA is subjected to a labeling treatment that results in the RNA in the sample of RNA being labeled with an observable label. A particularly contemplated labeling protocol is described in copending application Ser. No. 11/048,255 entitled "RNA Labeling Method" and filed by Wang on Jan. 31, 2005. In an embodiment, the digested RNA sample is labeled with an observable label after the RNA sample has been contacted with the enzyme having the DNA: RNA nuclease activity. Depending on the application, the presence of the observable label in the analogous DNA set may interfere with the analysis of the sample of RNA; therefore, in certain embodiments the analogous DNA set lacks the observable label.

In certain other embodiments, the analogous DNA set may be labeled with an observable label (possibly, though not necessarily, the same observable label used to label the RNA). In certain embodiments, the analogous DNA set may be labeled (i.e. the members of the analogous DNA set, e.g. the oligonucleotides, may be labeled) with a first observable label, such as Cy3, and the RNA sample may be labeled with a second observable label, such as Cy5, to give distinguishable signals upon observation of the labels. Such choice of first and second labels is referred to herein as "distinguishable" labels in that the labels that can be independently detected and measured, even when the labels are mixed. In other words, the amounts of label present (e.g., the amount of fluorescence) for each of the labels are separately determinable, even when the labels are co-located (e.g., in the same tube or in the same duplex molecule). Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), fluorescein and Texas red (Dupont, Boston, Mass.) and POPRO3 and TOPRO3 (Molecular Probes, Eugene, Oreg.). Further suitable distinguishable detectable labels may be described in Kricka et al. (Ann Clin Biochem. 39:114-29, 2002).

In some embodiments, only one observable label moiety is attached to a labeled polynucleotide (e.g. labeled RNA molecule or labeled DNA molecule). In such embodiments, the labeled polynucleotide will consist essentially of the polynucleotide labeled with a single label moiety (i.e. each labeled polynucleotide molecule will have only one observable label moiety attached—referenced herein as a "singly-labeled" polynucleotide). This potentially provides increased ease of use in quantitative methods using the labeled polynucleotide.

In other embodiments, a labeled polynucleotide (e.g. labeled RNA molecule or labeled DNA molecule) may have a plurality of observable label moieties. Thus, the labeled polynucleotide will consist essentially of the polynucleotide labeled with a plurality of label moieties. This increased labeling of the polynucleotide may provide for greater sensitivity in analyses using the labeled polynucleotide.

Also provided by the subject invention are kits for practicing the subject methods, as described above. The subject kits include at least an analogous DNA set. In certain embodiments the subject kits may also include reagents for isolating RNA from a source to provide the sample of RNA. In some embodiments the subject kits optionally also include reagents for labeling RNA, reagents for contacting the sample of RNA with the analogous DNA set, enzymes for use with the subject methods such as described above, control samples, etc. The various components of the kit may be present in separate containers or certain compatible components may be precombined into a single container, as desired.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a suitable material, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable material.

The practice of the present invention will employ, unless otherwise indicated, conventional techniques of synthetic organic chemistry, biochemistry, molecular biology, and the like, which are within the skill of the art. Such techniques are explained fully in the literature. Unless otherwise defined herein, all technical and scientific terms used herein have the same meaning as commonly understood by one of ordinary skill in the art to which the invention belongs. The description herein is put forth so as to provide those of ordinary skill in the art with a complete disclosure of the methods and compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

In particular embodiments the present invention thus provides methods of treating a sample of RNA to remove sequences of RNA that are complementary to small RNAs (i.e. "interfering sequences"). It is expected that the present invention may provide a more sensitive assay system for the detection of small RNA in samples of RNA. Such samples of RNA may be obtained from sources reflecting different developmental stages, tissue samples, disease states, as well as any individual and/or abnormal variations.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties, provided that, if there is a conflict in definitions, the definitions provided herein shall control.

What is claimed is:

1. A method of treating a sample of RNA, the method comprising:
   a) contacting the sample of RNA with an analogous DNA set to provide a DNA/RNA duplex, wherein the analogous DNA set comprises at least one DNA oligonucleotide comprising at least ten contiguous nucleotides of a small RNA in said sample, except that uracils in the sequence of said small RNA are substituted with thymines in said DNA oligonucleotide;
   b) contacting the DNA/RNA duplex with an enzyme having an RNase H activity to provide a digested RNA sample; and
   c) analyzing said digested RNA sample to detect said small RNA.

2. The method of claim 1, further comprising:
   contacting the digested RNA sample with an enzyme having a DNA nuclease activity to result in digestion of the analogous DNA set.

3. The method of claim 2, wherein said enzyme having a DNA nuclease activity is DNase I.

4. The method of claim 1, wherein said small RNA is selected from the group consisting of a short interfering RNA (sRNA), microRNA (miRNA), tiny non-coding RNA (tncRNA) and a small modulatory RNA (smRNA).

5. The method of claim 1, further comprising inactivating the enzyme having the RNase H activity after the digested RNA sample is provided.

6. The method of claim 1, further comprising separating the enzyme having the RNase H activity from the digested RNA sample.

7. The method of claim 1, wherein the analogous DNA set comprises a plurality of different oligodeoxynucleotides, each of the plurality of different oligodeoxynucleotides comprising a sequence analogous to a small RNA.

8. The method of claim 7, wherein each of the plurality of different oligodeoxynucleotides is at least about 8 bases long to about 100 bases long.

9. The method of claim 7, wherein each of the plurality of different oligodeoxynucleotides is at least about 10 bases long to about 50 bases long.

10. The method of claim 1, wherein the analogous DNA set comprises at least 5 different oligodeoxynucleotides, each of the oligodeoxynucleotides comprising a sequence analogous to a small RNA.

11. The method of claim 1, wherein the analogous DNA set comprises at least one oligodeoxynucleotide comprising a sequence analogous to a small RNA, wherein the sequence includes one or more base insertions, deletions and/or substitutions relative to the small RNA.

12. The method of claim 1, wherein the analogous DNA set comprises at least one polydeoxynucleotide having a plurality of small RNA complementary sequences.

13. The method of claim 1, wherein the enzyme having the RNase H activity is RNase H.

14. The method of claim 1, wherein the enzyme having the RNAse H activity is a thermostable RNase H.

15. The method of claim 1, further comprising, prior to contacting the sample of RNA with the analogous DNA set, labeling the sample of RNA with an observable label.

16. The method of claim 1, further comprising labeling the digested RNA sample with an observable label.

17. The method of claim 1, wherein the sample of RNA comprises RNA that has an observable label attached thereto.

18. The method of claim 14, wherein the analogous DNA set lacks the observable label.

* * * * *

UNITED STATES PATENT AND TRADEMARK OFFICE
CERTIFICATE OF CORRECTION

Page 1 of 1

PATENT NO. : 8,076,064 B2
APPLICATION NO. : 11/177679
DATED : December 13, 2011
INVENTOR(S) : Hui Wang It is certified that error appears in the above-identified patent and that said Letters Patent is hereby corrected as shown below:

On the Title page, in Item (56), under "Other Publications", in column 2, line 1, delete "Kamchatks" and insert -- Kamchatka --, therefor.

In column 17, line 49, in Claim 1, delete "oligonucleotide;" and insert -- oligonucleotide, and wherein said at least ten contiguous nucleotides are complementary and hybridize with RNA in said DNA/RNA duplex; --, therefor.

In column 17, line 51, in Claim 1, delete "to provide" and insert -- and thereby providing --, therefor.

In column 17, line 53, in Claim 1, delete "to detect" and insert -- and thereby detecting --, therefor.

In column 17, line 63, in Claim 4, delete "(sRNA)," and insert -- (siRNA), --, therefor.

In column 18, line 49, in Claim 8, delete "about 8" and insert -- 10 --, therefor.

In column 18, line 52, in Claim 9, after "least" delete "about".

Signed and Sealed this
Thirteenth Day of March, 2012

David J. Kappos
*Director of the United States Patent and Trademark Office*

SEQUENCE LISTING

<160> NUMBER OF SEQ ID NOS: 4

<210> SEQ ID NO 1
<211> LENGTH: 43

```
<212> TYPE: RNA
<213> ORGANISM: Artificial Sequence
<220> FEATURE:
<223> OTHER INFORMATION: Synthetic Oligonucleotide

<400> SEQUENCE: 1
uauccuccag uaacauguaa ugacgaaugg agggucuucu aau            43

<210> SEQ ID NO 2
<211> LENGTH: 40
<212> TYPE: RNA
<213> ORGANISM: Artificial Sequence
<220> FEATURE:
<223> OTHER INFORMATION: Synthetic Oligonucleotide

<400> SEQUENCE: 2
auugauauga cccagcauuc gucauuaugu uacuggaaua                40

<210> SEQ ID NO 3
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 3
ataaggtcat tgtattactg cttacgaccc agtatagtta                40

<210> SEQ ID NO 4
<211> LENGTH: 42
<212> TYPE: RNA
<213> ORGANISM: Artificial Sequence
<220> FEATURE:
<223> OTHER INFORMATION: Synthetic Oligonucleotide

<400> SEQUENCE: 4
auuacaagac cugcauucgu cguuaguugu uacuggacca ua             42
```